United States Patent [19]
Haynie et al.

[11] Patent Number: 5,599,689
[45] Date of Patent: Feb. 4, 1997

[54] PROCESS FOR MAKING 1,3-PROPANEDIOL FROM CARBOHYDRATES USING MIXED MICROBIAL CULTURES

[75] Inventors: Sharon L. Haynie, Philadelphia, Pa.; Lorraine W. Wagner, Newark, Del.

[73] Assignee: E. I. du Pont de Nemours and Company, Wilmington, Del.

[21] Appl. No.: 440,379

[22] Filed: May 12, 1995

[51] Int. Cl.$^6$ ................................................ C12P 39/00
[52] U.S. Cl. ........................................ 435/42; 435/158
[58] Field of Search ........................................ 435/42, 158

[56] References Cited

U.S. PATENT DOCUMENTS

| | | | |
|---|---|---|---|
| 4,935,554 | 6/1990 | Murphy et al. | 568/867 |
| 5,015,789 | 5/1991 | Arntz et al. | 568/862 |
| 5,254,467 | 10/1993 | Kretschmann et al. | 435/158 |

FOREIGN PATENT DOCUMENTS

| | | | |
|---|---|---|---|
| 0361082 | 4/1990 | European Pat. Off. | C12P 7/18 |
| 3533352 | 9/1985 | Germany . | |
| WO93/25696 | 12/1993 | WIPO | C12P 7/18 |

OTHER PUBLICATIONS

Forsberg, C. W., *Appl. and Environ. Microbiology*, 53(4), 639–643 (1987).

Sprenger, G. A. et al, *J. Gen. Microbiology*, 135, 1255–1262 (1989).

Agarwal, G. P. *Adv. Biochem. Eng./Biotechnol.*, 41(Microb. Bioprod., 95–127 (1990).

El-Kaddy, I. A. et al, *Folia Microbiol.*, 39(3), 203–207 (1994).

Nakas, J. P. et al, *Appl. and Enviorn. Micro.*, 46(5), 1017–1023 (1983).

Johnson, E. A. et al, *J. of Bacteriology*, 164(1), 479–483 (1985).

Daniel, R. et al, *FEMS Microbiology Letters*, 100, 281–286 (1992).

Bisping, B. et al, Appl. Microbiology and Biotechnology, 32, 119–123 (1989).

Tong, I-T et al, *Appl. Biochem. and Biotech.*, 34–35, 149–159 (1992).

Boenigk, R. et al, *App. Microbiology and Biotechnology*, 38, 453–457 (1993).

*Primary Examiner*—Herbert J. Lilling

[57] ABSTRACT

The present invention provides a process for the biotransformation of a carbohydrate carbon source to 1,3-propanediol using mixed yeast and bacterial cultures wherein the carbohydrate is first fermented to glycerol by the yeast cell and then converted to 1,3-propanediol by the bacterial cell containing an active diol or glycerol dehydratase enzyme in this process both the yeast and bacterial cultures are supported on the same carbon source, and 1,3-propanediol is isolated from the media.

1 Claim, No Drawings

PROCESS FOR MAKING 1,3-PROPANEDIOL FROM CARBOHYDRATES USING MIXED MICROBIAL CULTURES

FIELD OF INVENTION

The invention relates to the process of applying mixed or linked cultures in a fermentation to produce 1,3-propanediol. The invention also relates to the preparation of propanediol through glycerol from a carbohydrate source.

BACKGROUND OF THE INVENTION 1,3-Propanediol or trimethylene glycol is a valuable, but expensive chemical intermediate that is used as an additive to other substances or articles to enhance their physical properties or performance. 1,3-Propanediol is also used as a comonomer in the preparation of fiber and film-forming polymers. This chemical has found limited broad usage due to the high manufacturing costs associated with the feedstocks costs or the difficult process conditions.

Chemical preparation of 1,3-propanediol is known. For example ethylene oxide may be converted to 1,3-propanediol over a catalyst in the presence of phosphine, water, carbon monoxide, hydrogen and an acid. Alternatively 1,3-propanediol may be produced by the catalytic solution phase hydration of acrolein, or from hydrocarbons such as glycerol, reacted in the presence of carbon monoxide and hydrogen over catalysts from group VIII of the Periodic Table. These processes are energy intensive to run employing either high temperature or high pressure or both, resulting in a prohibitive costly process.

A microbiological or biochemical route to 1,3-propanediol, employing either metabolically-active microorganisms or the enzymes derived from biological sources, has been described. The process uses Enterobacter or Clostridium organism in a strict anaerobic habitat where glycerol is converted to 1,3-propanediol. The source or glycerol may be fossil fuels or from the water or residual waste stream from a distillery. Other organisms known to convert glycerol to propanediol are found e.g., in the species Klebsiella, Citrobacter, Clostridium, and Lactobacillus.

In addition to these native 1,3-propanediol producers recombinant organisms have also been constructed that convert glycerol to 1,3-propanediol. The genes responsible for the conversion of glycerol to 1,3-propanediol have been isolated and are all encompassed by the dha regulon. In order to make use of the advantages of higher protein expression and growth rate of recombinant bacteria, several attempts have been made to express the dha regulon as heterologous genes in *E. coli*. For example, the dha regulon from Citrobacter and Klebsiella have been expressed in *E. coli* and have been shown to convert glycerol to 1,3-propanediol. In one such system Tong et al., (Appl. Biochem. Biotech., 34, 149, (1992)) examined the improved production of 1,3-propanediol by cofermenting carbohydrates with glycerol.

In this system, a single organism uses the carbohydrate solely for a source of energy and enhanced cell growth. No propanediol was produced in the absence of exogenous glycerol. This study does not teach the conversion of carbohydrates into the carbon stream that produces 1,3-propanediol nor does it describe a mechanism for achieving this in a mixed culture as described in this Application.

Neither the chemical or biological methods described above for the production of 1,3-propanediol is well suited for industrial scale production since the chemical processes are energy intensive and the biological processes require the expensive starting material, glycerol. A method requiring low energy input and an inexpensive starting material is needed.

As with 1,3-propanediol, glycerol may be produced both by chemical and biological routes. Chemical processes generally employ petroleum-derived raw materials such as acrolein; allyl chloride; or propylene oxide and generally suffer from the same disadvantages as the chemical routes to 1,3-propanediol, including expensive raw materials or hazardous operating conditions.

Biological processes for the preparation of glycerol are known. The overwhelming majority of glycerol producers are yeasts but some bacteria, fungi and algae are also known. Bacteria, yeasts, and fungi produce glycerol by converting glucose or other carbohydrates through the fructose-1,6-bisphosphate pathway in glycolysis or the Embden Meyerhof Parnas pathway. Certain algae convert dissolved carbon dioxide or bicarbonate in the chloroplasts into the 3-carbon intermediates of the Calvin cycle. In a series of steps, the 3-carbon intermediate, phosphoglyceric acid, is converted to glyceraldehyde 3-phosphate which can be readily interconverted to its keto isomer, dihydroxyacetone phosphate, which is ultimately converted to glycerol. Although biological methods of both glycerol and 1,3-propanediol production are known, it has never been demonstrated that the two processes may be carried on together under the same reaction conditions. Such a process, utilizing mixed or linked cultures would represent an improvement in the production of 1,3-propanediol since it would be cost effective and would avoid the use of hazardous reagents.

The concept of successive or linked fermentations for biochemical transformations is known in the art and have been adapted for alcohol production. For example, Nakas et.al. (Appl. Environ. Microbiol. 46:1017–1023, 1983) describe a system for the production of mixed solvents of butanol, ethanol and 1,3-propanediol using a sequential fermentation process. The production system employs a photosynthetic algal genus, Dunaliella, to convert carbon dioxide to glycerol in a high salt medium. A *Clostridium pasterianum* strain was added to the $CO_2$-derived glycerol and algae mixture to produce a solvent blend that was primarily butanol.

The use of mixed cultures in industrial applications are known in the art but suffer from the requirement that each cell type be supported by a separate carbon substrate. So for example, yeast and lactic acid bacteria are used symbiotically in bread dough starter cultures. In these mixed systems there is no competition for the carbon substrate since the yeast uses only the glucose and the lactic acid bacterium uses only the maltose in the dough. Alternatively mixed culture systems have been developed where one organism produces a desirable effect in response to the presence of the other organism. So for example it has been demonstrated that in combinations of a bacterium (*B. subtilis*) with one of several yeasts, the induction of a bacterial protein was entirely dependent on the presence and concentration of a specific yeast in the medium. The increased sensitivity of yeasts to a specific class of antifungal agents when they are grown in mixed cultures with bacteria has been described.

Although applications of mixed cultures are known, it is a tenant of the art that the outcome in a mixed culture is not predictable. Mixed culture systems are particularly susceptible to complications caused by competition between organisms for the carbon source, diversion of the carbon out of the desired pathway, catabolite repression by the substrate, inhibition by the metabolites in the fermentation, and the difficulty in justifying the often highly dissimilar culture needs of each organism.

In spite of these difficulties in the use of mixed cultures, Applicants have succeeded in developing a mixed culture system that is capable of producing 1,3-propanediol from an unrefined carbohydrate source. Applicants have also devised a binary linked culture system for the production of 1,3-propanediol from a suitable carbon source. Applicants have overcome the difficulties of catabolite repression, feedback inhibition and carbon source diversion to create a system that is optimized for 1,3-propanediol production.

SUMMARY OF THE INVENTION

The present invention comprises a biological process for preparing 1,3-propanediol comprising the steps:

(a) contacting at least one carbon substrate having at least one carbon atom with a glycerol producing organism and with a diol producing organism to yield a medium;

(b) incubating said medium to produce propanediol.

In particular, the process of the present invention can be conducted via a mixed culture or a linked culture. For a mixed culture the process of the present invention comprises the steps of:

(a) mixing a glycerol producing organism at a cell density of at least $1 \times 10^6$ cells/ml and a diol producing organism at a cell ratio of glycerol producing organism to diol producing organism of at least 0.04 to 1.0 to yield a mixed culture medium;

(b) contacting said mixed culture medium with a carbon substrate having at least one carbon atom; and (c) incubating said mixed culture medium to produce 1,3-propanediol.

For a linked culture the process of the present invention comprises the steps of:

(a) contacting a glycerol producing organism with a carbon substrate having at least one carbon atom to yield a glycerol conditioned medium;

(b) inoculating a diol producing organism into said conditioned medium; and (c) incubating said diol producing organism in said conditioned medium to produce 1,3-propanediol.

The present invention further comprises the composition comprising the product of the above-noted processes.

BRIEF DESCRIPTION OF BIOLOGICAL DEPOSITS

Applicants have made the following biological deposits under the terms of the Budapest Treaty:

| Depositor Identification Reference | Int'l. Depository Designation | Date of Deposit |
|---|---|---|
| Echerichia coli, Dh5α, pKP1 | ATCC 69789 | 18 April 1995 |
| Echerichia coli, Dh5α, pKP4 | ATCC 69790 | 18 April 1995 |

The transformed E. coli pKP1 contains as portion of the Klebsiella genome encoding the glycerol dehydratase enzyme. The transformed E. coli pKP4 contains a portion of the Klebsiella genome encoding a diol dehydratase enzyme. As used herein, "ATCC" refers to the American Type Culture Collection international depository located at 12301 Parklawn Drive, Rockville, Md. 20852 U.S.A. The "ATCC No." is the accession number to cultures on deposit with the ATCC.

DETAILED DESCRIPTION OF THE INVENTION

As used herein the following terms may be used for interpretation of the claims and specification.

The term "1,3-propanediol" refers to a compound of the formula $HOCH_2-CH_2-CH_2OH$, useful as a monomer in the production of polymers for fiber manufacture. This compound is also commonly referred to as 1,3-dihydroxypropane, 1,3-propylene glycol, 1,3-propylenediol, or trimethylene glycol.

The term "glycerol producer" or "glycerol producing organism" refers to any cell type capable of producing glycerol. Cells capable of producing glycerol may be aerobic or anaerobic organisms of either bacterial, fungal, algal or yeast species.

The term "diol producer", "propanediol producer", "diol producing organism", or "propanediol producing organism" means any cell type that is capable of producing 1,3-propanediol utilizing glycerol. Generally, diol producing cells will contain either a diol dehydratase enzyme or a glycerol dehydratase enzyme.

The term "linked culture" means a fermentation system employing at least two cell cultures where the cultures are added sequentially. Generally in linked systems a primary culture or set of primary cultures are grown under optimal fermentation conditions for the production of a desired intermediate where that intermediate is produced in the media. Following fermentation with the primary culture, the conditioned media is then exposed to the secondary culture(s). The secondary cultures then convert the intermediate in the conditioned media to the desired end product. In the present application the primary cultures are typically glycerol producers and the secondary cultures are 1,3-propanediol producers.

The term "mixed culture" refers to any combination of microorganisms grown in the same reaction vessel where the interaction of the individual metabolic processes of the combined organisms results in a product which neither individual organism is capable of producing. Mixed cultures may be binary, tertiary or contain any number of individual species. Further mixed cultures may contain cells of divergent species.

The term "conditioned media" means any fermentation media suitable for the growth of microorganisms that has been supplemented by organic byproducts of microorganism growth. In the present invention conditioned media is produced during fermentation of linked cultures where glycerol producing cells secrete glycerol into the fermentation media for subsequent conversion to 1,3-propanediol.

The term "carbon substrate" means any carbon source capable of being metabolized by a microorganism wherein the substrate contains at least one carbon atom.

The term "dehydratase enzyme" refers to any enzyme that is capable of converting a glycerol molecule to the product hydroxypropionaldehyde. For the purposes of the present invention the dehydratase enzymes are either a glycerol dehydratase or a diol dehydratase having preferred substrates of glycerol and 1,2-propanediol, respectively.

The present invention comprises a process for the production of 1,3-propanediol involving the fermentation of a carbon substrate using mixed cultures. Cells of the mixed cultures are utilized on a carbon substrate, typically a carbohydrate, under controlled conditions to allow for the maximum production of 1,3-propanediol. The mixed cultures comprise cells of at least two different types. At least one cell type is capable of converting a carbon substrate to glycerol and the other cell type is capable of converting glycerol to 1,3-propanediol. The binary cultures are used either together or sequentially in a linked fermentation system and the conversion of carbohydrate to 1,3-propanediol occurs in one reaction vessel.

Cells:

Many cell types are know to produce glycerol and virtually any cell is suitable in the present invention. Typically glycerol producers utilize a variety of carbon sources including both carbohydrates and single carbon substrates. Typical glycerol producers that utilize a carbohydrate carbon substrate are either bacterial, fungal, or yeast cells and include but are not limited to members of the genera, Aspergillus, (*A. wentii*), Saccharomyces, (*S. cerevisiae*), Zygosaccharomyces, (*Z. rouxii*), Pichia, (*P. farinosa* and *P. miso*), Bacillus, (*B. licheniformis*), Kluyveromyces, (*K. marxianus*), Candida sp, Hansenula sp, Debaryomyces sp. and, Mucor, (*M. ruoxii*). Typical glycerol producers that utilize single carbon substrates are yeasts, bacteria, algae or fungi and include but are not limited to members of the genera Candida, Dunaliella sp., Hansenula, Pichia, Torulopsis, Saccharomyces, Methylobacteria, and Escherichia. Glycerol producers may also include recombinant organisms transformed with the necessary genes. Preferred for use in the present invention are yeast cells of the genus Saccharomyces where the species *S. cerevisiae* ATCC 64236 is most preferred.

Cells capable of producing 1,3-propanediol are known in the art. All diol producing organisms must contain an active dehydratase enzyme capable of converting glycerol through hydroxypropionaldehyde (3-HPA) to 1,3-propanediol. Cells containing this pathway may include natural organisms belonging to the genera Citrobacter, Enterobacter, Clostridium, Klebsiella, Lactobacillus or may include recombinant organisms transformed with the necessary genes. Preferred in the present invention are species of the genera Klebsiella or Citrobacter or a recombinant *E. coli* containing either a heterologous diol dehydratase enzyme or a glycerol dehydratase enzyme. Particularly preferred are recombinant *E. coli* DH5α strains pKP1 or pKP4

The cell density employed in the process of the present invention is from about $1\times10^6$ to about $1\times10^8$ cells/ml. When using the mixed culture the glycerol producing organism and the diol producing organism are present at a cell ratio of from about 0.04:1.0 to about 100:1, preferably from about 0.4:1.0 to about 5:1.

Recombinant Glycerol and Propanediol Producers:

Recombinant organisms containing the necessary genes that will encode the enzymatic pathway for the conversion of glycerol to 1,3-propanediol may be constructed using techniques well known in the art. In the present invention genes encoding either the glycerol dehydratase or the diol dehydratase pathway were isolated from a native host such as Klebsiella and used to transform the *E. coli* host strain DH5α.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202 issued in 1987 to Mullis, et al.) to obtain amounts of DNA suitable for transformation using appropriate vectors.

Alternatively cosmid libraries may be created where large segments of genomic DNA (35–45kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook, J. et al., *Molecular Cloning: A Laboratory Manual*, Second Edition (1989) Cold Spring Harbor Laboratory Press, herein incorporated by reference.

Typically to clone cosmids, foreign DNA is isolated and ligated, using the appropriate restriction endonucleases, adjacent to the cos region of the cosmid vector. Cosmid vectors containing the linearized foreign DNA is then reacted with a DNA packaging vehicle such as bacteriophage λ. During the packaging process the cos sites are cleaved and the foreign DNA is packaged into the head portion of the bacterial viral particle. These particles are then used to transfect suitable host cells such as *E. coli*. Once injected into the cell, the foreign DNA circularizes under the influence of the cos sticky ends. In this manner large segments of foreign DNA can be introduced and expressed in recombinant host cells.

Cosmid vectors and cosmid transformation methods were used within the context of the present invention to clone large segments of genomic DNA from bacterial genera known to possess genes capable of processing glycerol to 1,3-propanediol. Specifically, genomic DNA from *K. pneumoniae* and *K. aerogenes* was isolated by methods well known in the art and digested with the restriction enzyme Sau3A for insertion into a cosmid vector Supercos 1 and packaged using GigapackII™ packaging extracts. Following construction of the vector *E. coli* XL1-Blue MR cells were transformed with the cosmid DNA. Transformants were screened for the ability to convert glycerol to 1,3-propanediol by growing the cells in the presence of glycerol and analyzing the media for 1,3-propanediol formation.

The DNA sequences generated from cosmid transformations pKP4 was compared to DNA sequences in the Genbank data base. Several independent clones showing homology to cob region of *S. typhimurium* were identified suggesting that these transformants carried DNA encoding a 1,2-diol dehydratase gene. In addition, in transformant pKP1 an open reading frame that showed extensive homology to glycerol dehydratase gene from *C. freundii* suggesting that these transformants containing DNA encoding the glycerol dehydratase gene.

Mutants:

In addition to the cells exemplified it is contemplated that the present method will be able to make use of cells having single or multiple mutations specifically designed to enhance the glycerol or the 1,3-propanediol pathway. Cells that normally divert a carbon feed stock into non-productive pathways, or that exhibit significant catabolite repression could be mutated to avoid these phenotypic deficiencies. For example, in the present process cells of the genera Klebsiella and Citrobacter have been found to be particularly useful in the conversion of glycerol to 1,3-propanediol. However, these wildtype cells are also subject to catabolite repression from glucose in the media. Thus, mutant strains of these 1,3-propanediol producers that are resistant to glucose repression would be particularly useful in the present invention.

Methods of creating mutants are common and well known in the art. For example, wildtype cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989)Sinauer Associates, Inc., Sunderland, Mass., or Deshpande, Mukund V. Appl. Biochem. Biotechnol. 36, 227, (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See Brock, Supra., DeMancilha et al., Food Chem., 14, 313, (1984).

Fermentation Media:

Fermentation media in the present invention must contain suitable carbon substrates which will include but are not limited to monosaccharides such as glucose, oligosaccharides such as lactose or sucrose, polysaccharides such as starch or cellulose and unpurified mixtures from a renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. Glycerol production from single carbon sources (e.g., methanol, formaldehyde or formate) has also been reported in methylotrophic yeasts (K. Yamada et.al. Agric. Biol. Chem. 53(2) 541–543, 1989) and in bacteria (Hunter et.al., Biochemistry, 24, 4148–4155 (1985)]. These organisms can assimilate single carbon compounds, ranging in oxidation state from methane to formate, and produce glycerol. The pathway of carbon assimilation can be through ribulose monophosphate or through serine. The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd., [Int. Syrup. ], 7th (1993), 415–32. Editor(s): Murrell, J. Collin; Kelly, Don P. Publisher: Intercept, Andover, UK). Hence it is contemplated that the source of carbon utilized in the present invention may encompass a wide variety of carbon containing substrates and will only be limited by the choice of organism.

Although it is contemplated that all of the above mentioned carbon substrates are suitable in the present invention preferred are the carbohydrates glucose, fructose or sucrose. The concentration of the carbon substrate is from about 0.2% to about 30% on a weight/volume basis. Preferably, the concentration is from about 1.8% to about 9.0% on a weight/volume basis.

In addition to an appropriate carbon source, fermentation media must contain suitable minerals, salts, vitamins, cofactors and buffers suitable for the growth or the cultures and promotion of the enzymatic pathway necessary for 1,3-propanediol production.

Culture conditions:

Precultures:

Typically both glycerol producing cells and diol producing cells are grown separately as precultures and mixed at the beginning of fermentation. Cell cultures are grown at 30° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science.

Mixed Culture and linked Fermentations:

The process of the present invention is practiced using either mixed cultures or linked fermentation processes. Mixed cultures entail culturing both glycerol and diol producing cells in the same reaction vessel at the same time while linked fermentation employs sequentially added cultures.

The mixed culture method requires that both the glycerol and 1,3-propanediol producing cells are cultured under conditions and in fermentation media suitable for both cells. The glycerol-producing organism must be capable of fermenting whatever carbon substrate is fed in the fermentation. The propanediol-producing organism does not have to ferment the carbon substrate provided in the feed medium, but the propanediol-producing organism must sustain itself on at least one of the metabolic products formed in the fermentation by the glycerol-producing organism. Suitable pH ranges for the fermentation are between pH 5 to pH 8 where pH 7 to pH 7.5 is preferred as the initial condition. At the time of fermentation the glycerol producer and the diol producer are mixed to achieve a ratio in the range of 100:1 to 0.04:1, where 5:1 is preferred. It is preferred that the fermentation media are deaerated to provide anaerobic conditions necessary to optimize the production of propanediol; however, this invention is not limited to maintaining a strict anaerobic atmosphere.

Alternatively it can be useful to operate the present process in a linked microbial system as opposed to using mixed cultures. Linked systems generally involve the growing of a primary culture where a desired chemical intermediate is produced, removing the cells of the primary culture and then exposing the media to the secondary culture where the intermediate is then converted to the desired end product. The advantage that the linked system has over the mixed cultures is that control over fermentation conditions for each individual culture is simplified. For example, in linked culture systems each cell can be provided with the most appropriate carbon source and fermentation conditions for that organism and the difficulty of more than one cell competing for the same carbon source is removed. Thus media compositions can be tailored to maximize performance of the cells in either the primary or secondary cultures without the necessity of modifying one media to suit both cultures. The disadvantage of the linked system is that the reaction time needed to produce the end product is usually lengthened.

In the process of the present invention linked cultures were used successfully to convert sugars to 1,3-propanediol. Typically glycerol was produced by the primary cultures in standard fermentation media. Unlike in the mixed culture system, some of the glycerol producers were exposed to aerobic conditions to maximize glycerol production. Incubations ranged from 36 hr. to 48 hr. Following the fermentation by the primary glycerol producing cultures, the conditioned media was deaerated and diol producing cells were added to the conditioned media. Secondary cultures were incubated for between 20 and 24 hr.

Whether the present process employs mixed cultures or linked cultures the order of addition of the cells will affect propanediol yields. When the glycerol-producing organism is added before or at the same time as the propanediol-producing organism, the conversion of the carbon substrate to the propanediol-precursors is maximized. In mixed sytems where both organisms are added simultaneously, 1,3-propanediol is produced more quickly than when the organisms are added sequentially in the linked system. The 1,3-propanediol product can be formed early in the fermentation even though high glucose levels prevail. In preferred modes of operation, the polyhydroxyl product dominating the fermentation process is 1,3-propanediol.

It will be appreciated by one of skill in the art of fermentation microbiology that, now that Applicants have demonstrated the feasibility of the process of the present invention a number of factors affecting the fermentation processes may have to be optimized and controlled in order to maximize 1,3-propanediol production. Many of these factors such as pH, carbon source concentration, and dissolved oxygen levels may affect the enzymatic process depending on the cell types used for 1,3-propanediol production.

Cells used in successful mixed or linked fermentations of the present invention are able to be recycled and used in subsequent processes. Because these cell batches are typically at high densities and in a stationary growth phase it would appear that active growth is not a requirement for participation in the enzymatic process for the production of 1,3-propanediol.

Batch and Continuous Fermentations:

The present process employs a batch method of fermentation for both mixed and linked culture systems. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Identification and Purification of 1,3-propanediol:

Methods for the purification of 1,3-propanediol from fermentation media are known in the art. For example propanediols can be obtained from cell media by subjecting the reaction mixture to extraction with an organic solvent, distillation and column chromatography (U.S. 5356812). A particularly good organic solvent for this process is cyclohexane (U.S. 5008473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01N sulfuric acid in an isocratic fashion.

EXAMPLES

GENERAL METHODS

Materials and Methods suitable for the maintenance and growth of bacterial cultures were found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), pp. 210–213. American Society for Microbiology, Washington, DC. or Thomas D. Brock in Biotechnology: *A Textbook of Industrial Microbiology*, Second Edition (1989)Sinauer Associates, Inc., Sunderland, Mass. All reagents and materials used for the growth, and of bacterial cells were obtained from Diffco Laboratories (Detroit, Mich.), Aldrich Chemicals (Milwaukee, Wis.) or Sigma Chemical Company (St. Louis, Mo.) unless otherwise specified.

Growth medium for the precultures or inoculuum is commercially available and preparations such as Luria Bertani (LB) broth, Sabouraud Dextrose (SD) broth or Yeast medium (YM) broth are obtainable from GIBCO/BRL (Gaithersburg, Md.). LB-50amp is Luria-Bertani broth containing 50 µg/ml ampicillin.

Fermentation Media:

Two basic fermentation media were prepared for use in the following examples, and identified as Media A or B. These basic media were modified by altering the carbon source or by the addition of other reagents such as sulfite.

Medium A:

Medium A contained 100 mM glucose; 50 mM potassium phosphate, pH 7.5; 10 mM ammonium sulphate; 0.01% casamino acids; 0.01% yeast extract; 0.80 µg/ml vitamin B-12; 50 µg/ml ampicillin; and 1% S10 metal mix.

The S10 metal mix contained the following minerals at the indicated concentration:

200 mM $MgCl_2$; 70 mM $CaCl_2$; 5 mM $MnCl_2$; 100 µM $FeCl_3$; 100 µM $ZnCl_2$; 172 µM $CuSO_4$; 253 µM $COCl_2$; 242 µM sodium molybdate; 200 µM thiamine hydrochloride.

Medium A/S:

This media consisted of medium A modified with sodium sulfite at a concentration of 56.7 mM or (72 mg solid $Na_2SO_3$ per 10 ml reaction; 4 g solid $Na_2SO_3$ per 10 g glucose).

Medium B:

Medium B differed from medium A only in that it contained 200 mM glucose as opposed to 100 mM glucose.

In examples assessing the effect of alternate carbon sources on the production of 1,3-propanediol Medium A or A/S was used and the substitutions are indicated in the respective examples.

Cells:

All commercially available cells used in the following examples were obtained from the ATCC and are identified in the text by their ATCC number. Four recombinant *E. coli* DH5α cells were used as diol producers and were identified as pKP1, pKP2, pKP4, and pKP5. Sequence analysis revealed that the strains pKP1 and pKP2 contained genes encoding the glycerol dehydratase enzyme whereas strains pKP4 and pKP5 contained genes encoding the diol dehydratase enzyme.

1,3-propanediol analysis:

All fermentation mixtures were analyzed by HPLC on an analytical ion exchange column (HPX-87H, 4.6 mm×25 cm equipped with a Hi-Pore Cation H precolumn, BioRad Corp., Richmond, Calif.), using a Waters Millennium 2010 HPLC system composed of two Model 510 pumps, Model 490E multiwavelength detector, Model 717 autosampler, column heater and a Millennium 2010 chromatography manager with a pump control module (Waters Chromatography Division, Marlborough, Mass.). The fermentation alcohols and acids were eluted by an isocratic method that involved the elution of a running phase of 0.010N sulfuric acid at a flow rate of 1.0 ml/min at 50° C. The compounds were confirmed by comparison against external standards.

1,3-Propanediol was verified by running a gas chromatography/mass spectrometer (GC/MS) analysis. Samples (1 µl) were injected splitless onto a DB17 column (30 m×0.25 mm i.d., 0.25µ film thickness, J & W Scientific (Folsom, Calif.) in a Hewlett Packard 5890 Series gas chromatography with a Hewlett-Packard 5971 Series mass selective detector (Hewlett-Packard Analytical Div., Wilmington, Del.). The retention time and the mass fragmentation pattern of controls were determined and compared to those of the samples.

EXAMPLE 1

Preparation of mixed cultures

The mixed cultures were prepared by growing each organism as a preculture at 30° C. with shaking (250 rpm). In a sterile 1-L sterile flask, an inoculum of frozen *S. cerevisiae* cells and 200 ml SD broth were grown overnight in an New Brunswick Scientific Series G25 incubator/shaker (Edison, N.J.). The cells were grown until the optical density readings (Cary 219 UV/Vis spectrophotometer (Sunnyvale, Calif.) or Klett-Sommerson photoelectric colorimeter (New York, N.Y.)) were constant with time. *K. pneumoniae* or *C. freundii* were grown overnight by inoculating 100 mls of LB broth with a frozen stock of the cells. The recombinant *E. coli* propanediol producers were grown overnight by inoculating a frozen cell stock into 100 mls of LB-50 amp. These precultured cell suspensions either were used directly in the fermentations or were centrifuged and the pellets were resuspended in a much smaller volume of fermentation medium. In the following examples, the glycerol-producing organism, *S. cerevisiae*, was present at an initial cell concentration in the fermentation that ranged from $1\times10^6$ to $5\times10^8$ cells ml$^{-1}$; the propanediol producing organism (recombinant *E. coli*, *K. pneumoniae*, or *C. freundii*) was present at an initial cell concentration in the fermentation that ranged from $1\times10^6$ to $5\times10^8$ cells ml$^{-1}$). The mixed culture was prepared by mixing the two cells so that the ratio of their concentrations achieved the proportion specified in the example.

The cells could be reused by suspending the cell paste recovered from a fermentation into phosphate buffer and storing either at 4° C. (short term) or at −70° C. (long term). The cells were washed before reuse.

EXAMPLES 2–34

Batch fermentations on glucose

The following examples illustrate the preparation of 1,3-propanediol using a mixed culture and glucose as the carbon source.

A 50-ml erlenmeyer flask was charged with 10 ml of either medium A, A/S, or B depending on the experiment. Prior to mixing, the medium and the precultures were deaerated with argon or nitrogen. The organisms were added simultaneously from fresh precultures. After the cells had been added to the reaction medium, the reaction contents and vessel were sparged with argon or nitrogen prior to capping the vessel. The flask was incubated at 30° C. in a New Brunswick G25 shaker incubator and rotated at 250 rpm. The reaction vessel was sampled periodically and tested for glycerol and 1,3-propanediol production by HPLC. Fermentations were typically run for 24 to 48 hours.

The fermentation mixtures were analyzed by HPLC and confirmed by G/C MS as described in the GENERAL METHODS.

Data demonstrating the production of 1,3-propanediol from glucose in a mixed culture fermentation is shown in Table 1, below.

TABLE 1

| | Processes Yielding 1,3-Propanediol From Mixed Cultures Fermenting on Glucose | | | | |
|---|---|---|---|---|---|
| Ex. # | Glycerol-producer (A) | 1,3-Propanediol-producer(B) | A:B$^a$ | Yield$^b$(g) | Conditions (Medium; T (°C.); time (h)) |
| 1 | S. cerevisiae ATCC 64236 | — | | 0 | A; 30; 48 |
| 2 | — | E. coli DH5α pKP1 | | 0 | A; 30; 48 |
| 3 | S. cerevisiae ATCC 64236 | E. coli DH5α pKP1 | 0.04 | 2.9 | B; 26; 15 |
| 4 | S. cerevisiae ATCC 64236 | E. coli DH5α pKP1 | 0.2 | 4.77 | A; 30; 48 |
| 5 | S. cerevisiae ATCC 64236 | E. coli DH5α pKP1 | 5 | 8.8 | A; 30; 48 |
| 6 | S. cerevisiae ATCC | E. coli DH5α pKP1 | 25 | 7.1 | A; 30; 48 |

TABLE 1-continued

Processes Yielding 1,3-Propanediol From Mixed Cultures Fermenting on Glucose

| Ex. # | Glycerol-producer (A) | 1,3-Propanediol-producer(B) | A:B[a] | Yield[b](g) | Conditions (Medium; T (°C.); time (h)) |
|---|---|---|---|---|---|
| 7 | S. cerevisiae ATCC 64236 | E. coli DH5α pKP1 | 100 | 3.97 | A$_{500}$[c]; 35; 50 |
| 8 | S. cerevisiae ATCC 64236 | E. coli DH5α pKP4 | 0.2 | 5.0 | B; 26; 39 |
| 9 | S. cerevisiae ATCC 64236 | E. coli DH5α pKP5 | 0.2 | 2.14 | A; 30; 48 |
| 10 | S. cerevisiae ATCC 64236 | E. coli ECL707 pKP1 | 0.2 | 4.36 | A; 30; 48 |
| 11 | S. cerevisiae ATCC 64236 | E. coli ECL707 pKP2 | 0.2 | 3.86 | A; 30; 48 |
| 12 | S. cerevisiae ATCC 64236 | E. coli 707 pKP4 | 0.2 | 1.32 | A; 30; 48 |
| 13 | — | C.freundii ATCC 8454 |  | 0 | A; 30; 48 |
| 14 | S. cerevisiae ATCC 64236 | C.freundii ATCC 8454 | 0.2 | 2.23 | A; 30; 48 |
| 15 | S. cerevisiae ATCC 64236 | C.freundii ATCC 8454 | 5 | 10.3 | A; 30; 48 |
| 16 | — | K. pneumoniae ATCC 25955 |  | 0 | A; 30; 48 |
| 17 | S. cerevisiae ATCC 64236 | K. pneumoniae ATCC 25955 | 0.2 | 3.0 | A; 30; 48 |
| 18 | S. cerevisiae ATCC 64236 | K. pneumoniae ATCC 25955 | 25 | 10.3 | A; 30; 48 |
| 19 | S. cerevisiae ATCC 64236 | K. pneumoniae ATCC 25955 | 5 | 10.1 | A/S; 30; 48 |
| 20 | S. cerevisiae ATCC 4132 | — |  | 0 | A; 30; 48 |
| 21 | S. cerevisiae ATCC 4132 | E coli DH5α pKP1 | 0.2 | 2.4 | A; 30; 24 |
| 22 | S. cerevisiae ATCC 4132 | C.freundii ATCC 8454 | 0.2[d] | 3.3 | A; 30; 48 |
| 23 | S. cerevisiae ATCC 4132 | C.freundii ATCC 8454 | 5 | 5.5 | A; 30; 48 |
| 24 | S. cerevisiae ATCC 4132 | K. pneumoniae ATCC 25955 | 0.2 | 3.9 | A; 30; 24 |
| 25 | S. cerevisiae ATCC 4132 | K. pneumoniae ATCC 25955 | 25 | 4.8 | A; 30; 48 |
| 26 | P. miso ATCC 20210 | — |  | 0 | A; 30; 92 |
| 27 | P. miso ATCC 20210 | E coli DH5α pKP1 | 0.2 | 2.5 | A; 30; 92 |
| 28 | P. miso ATCC 20210 | E coli DH5α pKP1 | 25 | 7.6 | A; 30; 92 |
| 29 | P. miso ATCC 20210 | C.freundii ATCC 9454 | 5 | 1.56 | A; 30; 92 |
| 30 | P. miso ATCC 20210 | K. pneumoniae ATCC 25955 | 25 | 2.44 | A; 30; 92 |
| 31 | Z. rouxii ATCC | — |  | 0 |  |

TABLE 1-continued

Processes Yielding 1,3-Propanediol From Mixed Cultures Fermenting on Glucose

| Ex. # | Glycerol-producer (A) | 1,3-Propanediol-producer(B) | A:B[a] | Yield[b](g) | Conditions (Medium; T (°C); time (h)) |
|---|---|---|---|---|---|
| 32 | Z. rouxii ATCC 13356 | E coli DH5α pKP1 | 5 | 2.2 | A; 30; 48 |
| 33 | Z. rouxii ATCC 13356 | C.freundii ATCC 8454 | 5 | 4.0 | A; 30; 48 |
| 34 | Z. rouxii ATCC 13356 | K. pneumoniae ATCC 25955 | 5 | 2.5 | A; 30; 48 |

[a]initial cell concentration of glycerol producer (A) was between $1 \times 10^8$ to $5 \times 10^8$ cells ml$^{-1}$ for all examples unless otherwise noted
[b]Yield in grams (g) of 1,3-propanediol as determined by the following expression: (grams 1,3-propanediol produced)/(100 grams glucose consumed)
[c]$A_{500}$ medium containing 500 mM glucose and all the nutrients, salts, and vitamins described for medium A.
[d]The initial cell concentration of glycerol producer or A was $1 \times 10^7$ cells ml$^{-1}$ As can be seen from the data in Table 1, the ratio of and the particular blend of glycerol and 1,3-propanediol producing organisms were determinants in the yields of propanediol.

EXAMPLE 35–51

Fermentations on various carbohydrates

The following examples illustrate the preparation of 1,3-propanediol using a mixed culture where the glycerol producing cell was always S. cerevisiae and the diol producer was varied. This example analyzed the effect of altering the carbon source in these mixed cultures.

All cells were cultured and fermented in batch and experiments were run as described above in Examples 3–34. The medium contained all of the components described in medium A or medium A/S except that the indicated carbohydrate was substituted for glucose: medium F, 100 mM fructose; medium L, 50 mM lactose; medium S, 50 mM sucrose; medium M, 100 mM maltose.

Table 2 contains data showing the effect of varying carbon source on the production of 1,3-propanediol. The glycerol producer S. cerevisiae is abbreviated "SC6". The diol producers E. coli DH5α pKP1, Klebsiella pneumoniae and Citrobacter freundii, are abbreviated "EC", "KP" and "CF" respectively.

TABLE 2

| Ex. # | Carbohydrate; Medium | Cells A, B | A:B[a] | Yields[b] (g) | Yields[c] (Carbon) |
|---|---|---|---|---|---|
| 35 | sucrose; S | SC6, EC | 0.2 | 8.2 | 9.3 |
| 36 | lactose; L | SC6, EC | 0.2 | 3.4 | 3.8 |
| 37 | fructose; F | SC6, EC | 0.2 | 9.1 | 10.9 |
| 38 | maltose; M | SC6, EC | 0.2 | 2.3 | 2.6 |
| 39 | glucose; A | SC6, EC | 0.2 | 2.4 | 2.9 |
| 40 | glucose; A | SC6, CF | 5 | 1.1 | 1.3 |
| 41 | glucose; A | SC6, KP | 5 | 6.4 | 7.6 |
| 42 | fructose; F | SC6, CF | 5 | 7.7 | 9.2 |
| 43 | fructose; F | SC6, KP | 5 | 11.3 | 13.5 |
| 44 | sucrose; S | SC6, CF | 5 | 2.4 | 2.7 |
| 45 | sucrose; S | SC6, KP | 5 | 6.6 | 7.5 |
| 46 | glucose; A/S | SC6, CF | 5 | 10.1 | 12.0 |
| 47 | glucose; A/S | SC6, KP | 5 | 7.3 | 8.7 |
| 48 | fructose; F/S | SC6, CF | 5 | 11.9 | 14.2 |
| 49 | fructose; F/S | SC6, KP | 5 | 13.6 | 16.2 |
| 50 | sucrose; S/S | SC6, CF | 5 | 13.5 | 15.3 |
| 51 | sucrose; S/S | SC6, KP | 5 | 16.1 | 18.2 |

[a]The initial cell concentration of glycerol producer (A) was ca. $1 \times 10^7$ ml$^{-1}$ for Examples 35 through 39; the initial cell concentration of glycerol producer (A) was $5 \times 10^8$ cells ml$^{-1}$ for examples 40 through 51
[b]Yield in grams (g) of 1,3-propanediol as determined by the following expression: (grams 1,3-propanediol produced)/(100 grams carbohydrate consumed)
[c]Yield of propanediol expressed as: (carbon equivalents (moles) of 1,3-propanediol produced)/(carbon equivalents (moles) of carbohydrate consumed)

As can be seen by the data in Table 2, fructose and sucrose were preferred substrates in the absence of sulfite in the medium. The addition of sulfite in the medium significantly improved the yields of the intermediate, glycerol, and subsequently, the yields of 1,3-propanediol.

EXAMPLE 52–59

Fed-Batch Fermentations On Carbohydrates

The following examples illustrate the preparation of large quantities of 1,3-propanediol in high concentrations by using a Fed-Batch fermentation procedure. In this example a carbohydrate carbon source was added either in a single dose or as successive batches over time. The cells were either prepared fresh or the mixed culture cell paste was recovered from a previous fermentation. The initial cell concentration of S. cerevisiae was ca. $1.5 \times 10^8$ cells ml$^{-1}$; the initial cell concentration of the K. pneumoniae was ca. $3 \times 10^7$ cells ml$^{-1}$. The fermentations were initiated by transferring the cells into a 2-L reaction vessel containing i liter of medium. The vessel and the liquid contents were deaerated before transfer to an incubator/shaker at 30° C. The fermentation was run for 24 hours before addition of successive batches of solid carbohydrate which were added periodically.

TABLE 3

Large-Scale Batch or Fed-Batch Processes Yielding 1,3-Propanediol From Mixed Cultures Fermenting on Various Carbohydrates

| Ex. # | Type | Medium | Cells | Carbohydrate[a] (g/L) | 1,3-Propane-diol[b] (g/L) | Yield[c] (carbon) |
|---|---|---|---|---|---|---|
| 52 | batch | F/S | fresh | 18 | 1.75 | 11.57 |
| 53 | batch | F | fresh | 18 | 0.872 | 5.76 |
| 54 | batch | F | recycled | 18 | 1.23 | 8.13 |
| 55 | fed-batch | G | recycled | 45.3 | 2.27 | 5.96 |
| 56 | fed-batch | G/S | recycled | 45.4 | 3.4 | 8.9 |
| 57 | fed-batch | G/S | recycled | 92.6 | 4.78 | 6.14 |
| 58 | fed-batch | S/S | fresh | 34.2 | 3.75 | 12.3 |
| 59 | batch | S/S | fresh | 17 | 1.28 | 8.4 |

[a]The concentration in grams/liter of carbohydrate consumed in the reaction
[b]Concentration in grams/liter of 1,3-propanediol produced in the reaction
[c]Yield of 1,3-propanediol expressed as: (carbon equivalents (moles) of 1,3-propanediol produced)/(carbon equivalents (moles) of carbohydrate consumed)

EXAMPLES 60–60

Linked fermentations

The first stage or glycerol-producing stage was performed in medium C. Prior to the beginning the second stage, the fermentation medium was deaerated with nitrogen or argon and the pH was readjusted to 7. The second-stage was initiated with the addition of the preculture of the propanediol-producing organism at a final concentration of between $1 \times 10^6$ to $1 \times 10^7$ cells/ml in the fermentation. The addition of other nutritional agents such as thiamine or cyanocobalamin (vitamin B-12) was not required.

TABLE 4

Two-Stage Batch Fermentation Processes Yielding 1,3-Propanediol

| Ex. # | First Stage[a] | Second Stage[b] | Yield[c] | Yield[d] |
|---|---|---|---|---|
| 60 | aerobic, 46 hr, 30° C. S. cerevisiae ATCC 4132 | anaerobic, 22 hr, 30° C. K. pneumoniae ATCC 25955 | 3.0 | 3.6 |
| 61 | anaerobic, 38 hr, 30° C. S. cerevisiae ATCC 64236 | anaerobic, 23 hr, 30° C. K. pneumoniae ATCC 25955 | 4.12 | 4.9 |
| 62 | aerobic, 46 hr S. cerevisiae ATCC 64236 | anaerobic, 22 hr K. pneumoniae ATCC 25955 | 1.88 | 2.24 |
| 63 | aerobic, 38 hr S. cerevisiae ATCC 64236 | anaerobic, 23 hr K. pneumoniae ATCC 25955 | 4.17 | 4.9 |
| 64 | aerobic, 61 hr S. cerevisiae ATCC 4132 | anaerobic, 32 hr K. pneumoniae ATCC 25955 | 6.74 | 8.0 |
| 65 | anaerobic, 61 hr S. cerevisiae ATCC 4132 | anaerobic, 32 hr K. pneumoniae ATCC 25955 | 3.1 | 3.7 |

[a]The initial cell concentration of glycerol producer was ca. $1 \times 10^7$ cells ml$^{-1}$
[b]initial cell concentration of 1,3-propanediol producer was ca. $2 \times 10^8$ cells ml$^{-1}$
[c]Yield in grams (g) of 1,3-propanediol as determined by the following expression: (grams 1,3-propanediol produced)/(100 grams carbohydrate consumed)
[d]Yield of 1,3-propanediol expressed as: (carbon equivalents (moles) of propanediol produced)/(carbon equivalents (moles) of carbohydrate consumed)

Zygosaccharomyces, Pichia, Bacillus, Kluyveromyces, Candida sp., Hansenula sp., Dunaliella sp., Debaryomyces sp., Mucor, Torulopsis, Methylobacteria, Escherichia, and recombinant organisms transformed with the genes necessary for glycerol production, and wherein said diol-producing organism is selected from the group consisting of members of the genera Citrobacter, Enterobacter, Clostridium, Klebsiella, Lactobacillus, recombinant organisms transformed with a gene encoding a diol dehydratase enzyme or a glycerol dehydratase enzyme, and mutants having phenotypes which enhance production of 1,3-propanediol;

(b) contacting said mixed culture medium with a carbon substrate having at least a single carbon atom selected from the group consisting of monosaccharides, oligosaccharides, polysaccharides, carbon dioxide, methanol, formaldehyde, formate, and carbon-containing amines;

(c) incubating said mixed culture medium under suitable conditions to produce 1,3-propanediol; and (d) recovering said 1,3-propanediol.

What is claimed is:

1. A biological process for preparing 1,3-propanediol comprising the steps of:
   (a) mixing a glycerol-producing organism at a cell density of at least $1 \times 10^6$ cells/ml and a diol-producing organism at a cell ratio of glycerol-producing organism to diol-producing organism of at least 0.04 to 1.0 to yield a mixed culture medium, wherein said glycerol-producing organism is selected from the group consisting of members of the genera Aspergillus, Saccharomyces,

* * * * *